US008580261B2

(12) United States Patent
Lillard, Jr. et al.

(10) Patent No.: US 8,580,261 B2
(45) Date of Patent: *Nov. 12, 2013

(54) METHODS FOR PREVENTION AND TREATMENT OF INFLAMMATION USING ANTI-CHEMOKINE ANTIBODIES

(75) Inventors: James W. Lillard, Jr., Smyrna, GA (US); Udai P. Singh, Atlanta, GA (US); Shailesh Singh, Atlanta, GA (US); Jonathan Stiles, Powder Springs, GA (US)

(73) Assignee: Morehouse School of Medicine, Atlanta, GA (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/538,355

(22) Filed: Jun. 29, 2012

(65) Prior Publication Data

US 2012/0315272 A1 Dec. 13, 2012

Related U.S. Application Data

(63) Continuation of application No. 13/104,654, filed on May 10, 2011, which is a continuation of application No. 10/712,393, filed on Nov. 14, 2003, now Pat. No. 7,964,194.

(60) Provisional application No. 60/426,350, filed on Nov. 15, 2002, provisional application No. 60/426,347, filed on Nov. 15, 2002.

(51) Int. Cl.
*A61K 39/00* (2006.01)
*A61K 39/395* (2006.01)

(52) U.S. Cl.
USPC .................. 424/133.1; 424/158.1; 424/141.1; 424/145.1

(58) Field of Classification Search
None
See application file for complete search history.

(56) References Cited

U.S. PATENT DOCUMENTS

| | | | |
|---|---|---|---|
| 6,329,159 B1 * | 12/2001 | Andrew et al. | 435/7.24 |
| 6,329,510 B1 | 12/2001 | Qin et al. | |
| 6,936,248 B1 * | 8/2005 | Andrew et al. | 424/143.1 |
| 7,381,412 B2 * | 6/2008 | Andrew et al. | 424/141.1 |
| 2003/0166589 A1 | 9/2003 | Karin | |

FOREIGN PATENT DOCUMENTS

WO 02/15932 A1 2/2002

OTHER PUBLICATIONS

Papadakis et al., (Gastroenterology. Aug. 2001;121(2):246-54, Abstract Only).*
International Search Report (Application No. PCT/US2003/036556, filed Nov. 14, 2003).
Angostini, C., et al., "CXCR3 and Its Ligand CXCL10 Are Expressed by Inflammatory Cells Infiltrating Lung Allografts and Mediate Chemotaxis of T Cells at Sites of Rejection", American Society for Investigative Pathology, vol. 158, pp. 1703-1711 (2001).

* cited by examiner

*Primary Examiner* — Cherie M Stanfield
(74) *Attorney, Agent, or Firm* — Ping Wang; Andrews Kurth LLP

(57) ABSTRACT

It is possible to inhibit inflammatory processes by administration of antibodies to chemokines. Identification of chemokines which are over-produced makes it possible to block specific chemokine activity using antibodies to the over-expressed chemokines.

16 Claims, No Drawings

METHODS FOR PREVENTION AND TREATMENT OF INFLAMMATION USING ANTI-CHEMOKINE ANTIBODIES

This application is a continuation application of U.S. patent application Ser. No. 13/104,654, filed on May 10, 2011, which is continuation application of U.S. patent application Ser. No. 10/712,393, filed on Nov. 14, 2003, now U.S. Pat. No. 7,964,194 which claims priority of U.S. Provisional Application No. 60/426,350, and U.S. Provisional Application No. 60/426,347 both of which were filed on Nov. 15, 2002. The entirety of all of the aforementioned applications is incorporated herein by reference.

This work was partially supported by the U.S. Government. Hence, certain rights belong to the government.

FIELD

This invention relates to antibodies or the use of antibodies directed against certain chemokines. The antibodies block high-affinity interactions leading to inflammation.

BACKGROUND

Despite recent advances in studies related to the inflammation process, therapies for treatment of chronic inflammatory diseases have remained elusive. This is perhaps a result of the many and complex factors in the host that initiate and maintain inflammatory conditions. Current therapies have disadvantages associated with them, including the suppression of the immune system that can render the host more susceptible to bacterial, viral and parasitic infections. For example, use of steroids is a traditional approach to chronic inflammation treatment. Such treatment can lead to changes in weight and suppression of protective immunity. Advances in biotechnology have promoted the development of targeted biologicals with fewer side effects. To improve inflammatory disease treatment, technologies that alter and control the factors generated by cells of both innate and adaptive immunity systems need to be developed.

Host cells have surface receptors that associate with ligands to signal and regulate host cell activities. Administration of anti-TNF-α antibody or soluble TNF-α receptor has been shown to inhibit inflammatory diseases. Unfortunately, the side effects associated with this treatment can result in an increased risk of infections (e.g., tuberculosis) and other adverse reactions by mechanisms not fully understood. Similarly, antibody therapies focused on membrane bound molecules like CD40 have a propensity for inhibiting inflammation and graft-host diseases. While other targeted host cell therapies to prevent inflammatory diseases are being developed, there is no known single surface or secreted factor that will stop all inflammatory diseases. Consequently, the development of therapies to exploit newly identified specific host cell targets is required.

A variety of pathogens or toxins activate macrophages, neutrophils, T cells, B cells, monocytes, NK cells, Paneth and crypt cells, as well as epithelial cells shortly after entry into the mucosa. Chemokines are a superfamily of small, cytokine-like proteins that are resistant to hydrolysis, promote neovascularization or endothelial cell growth inhibition, induce cytoskeletal rearrangement, activate or inactivate lymphocytes, and mediate chemotaxis through interactions with G-protein-coupled receptors. Chemokines can mediate the growth and migration of host cells that express their receptors. The cellular mechanisms responsible for the function of chemokines are often, but not entirely, $Ca^{2+}$ flux dependent and pertussis toxin-sensitive. However, the precise mechanisms for chemokine-mediated events are not known.

SUMMARY

The present invention provides a means of inhibiting inflammation by administering anti-chemokine antibodies. Exemplified are anti-CXCL9, -CXCL10, -CXCL11, -CCRL1, -CCRL2, -CCR5, -CCL1, -CCL2, -CCL3, -CCL4, -CCL4L1, -CCL5, -CCL7, -CCL8, -CCL14-1, -CCL14-2, -CCL14-3, -CCL15-1, -CCL15-2, -CCL16, -CCL19, -CCL23-1, -CCL23-2, -CCL24, -CCL26, -CCR6, -CCL20, and -CCL25, -CCL25-1, -CCL25-2 antibodies. These chemokines are known. The Genbank assession numbers are provided herein. The invention utilizes antibodies or functional fragments thereof that bind to the target chemokines. The antibodies or antigen-binding fragment(s) bind to epitope(s) or peptide(s) that consists of 10 to 15 amino acids from sequences 1 through 30 (accession numbers in NIH-NCBI Genebank given below) of the target chemokines. Antibodies which act as modulators can administered mucosally or systemically.

The antibody, antibodies, or antigen-binding fragment or fragments can be isolated from the serum of immunized mammalian hosts, from cultures of immortalized cell lines and tissues such as hybridomas, lymphoblastoid or cells generated by methods of recombinant molecule biology. For increased effectiveness, fragments may be conjugated or linked to other peptides, proteins, nucleic acid sequences, vitamins, complex or simple carbohydrates, or other suitable carrier molecules.

Antibodies or antigen-binding fragments with specificity for functional mutant or variant mammalian chemokines are appropriate. These mutations or polymorphisms occur in nature or can be induced by recombinant molecular biological methods to generate single, multiple, or continuous amino acid residues, described in sequences 1 through 30, that are deleted, added, and/or substituted for other or no amino acids.

The mucosal means of application include oral, intranasal, ocular, intravaginal, rectal, and/or intraurethral administration in liquid or particulate form or on solid supports. Systemic means of application include parenteral, intravenous, or intramuscular administration in liquid or particulate form.

DETAILED DESCRIPTION

The invention provides methods of identifying, evaluating and treating a subject suffering from conditions arising from inflammatory processes, including anaphylaxis and septic shock, arthritis (e.g., osteoarthritis, rheumatoid, psoriatic), asthma, allergies (e.g., drug, insect, plant, food), atherosclerosis, delayed type hypersensitivity, dermatitis, diabetes (e.g., mellitus, juvenile onset), graft rejection, inflammatory bowel diseases (e.g., Crohn's disease, ulcerative colitis, enteritis), interstitial cystitis, multiple sclerosis, myasthemia gravis, Grave's disease, Hashimoto's thyroiditis, pneumonitis, prostatitis, psoriasis, nephritis, pneumonitis, chronic obstructive pulmonary disease, chronic bronchitis rhinitis, spondyloarthropathies, scheroderma, systemic lupus erythematosus, or throiditis using the said embodiments. As a result one or more of inflammatory processes including host cell migration or excretion.

It has now been demonstrated, using as examples anti-CXCL9, -CXCL10, -CXCL11, -CCRL1, -CCRL2, -CCR5, -CCL1, -CCL2, -CCL3, -CCL4, -CCL4L1, -CCL5, -CCL7, -CCL8, -CCL14-1, -CCL14-2, -CCL14-3, -CCL15-1, -CCL15-2, -CCL16, -CCL19, -CCL23-1, -CCL23-2, -CCL24, -CCL26, -CCR6, -CCL20, and -CCL25, -CCL25-1, -CCL25-2 antibodies, that it is possible to inhibit the inflammatory cell activation, migration or chemotaxis of the by inflammatory processes.

Materials and Methods

Primer Design

Messenger RNA sequences for CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 were obtained from the NIH-NCBI gene bank database (Sequences 31 through 60, accession numbers given later). Primers were designed using the BeaconJ 2.0 computer program. Thermodynamic analysis of the primers was conducted using computer programs: Primer Premier) and MIT Primer 3. The resulting primer sets were compared against the entire human genome to confirm specificity.

Real Time PCR Analysis

Lymphocytes or inflamed tissues were cultured in RMPI-1640 containing 10% fetal calf serum, 2% human serum, supplemented with non-essential amino acids, L-glutamate, and sodium pyruvate (complete media). Additionally, primary inflammatory and normal-paired matched tissues were obtained from clinical isolates (Clinomics Biosciences, Frederick, Md. and UAB Tissue Procurement, Birmingham, Ala.). Messenger RNA (mRNA) was isolated from $10^6$ cells using TriReagent (Molecular Research Center, Cincinnati, Ohio) according to manufacturers protocols. Potential genomic DNA contamination was removed from these samples by treatment with 10 U/µl of RNase free DNase (Invitrogen, San Diego, Calif.) for 15 minutes at 37° C. RNA was then precipitated and resuspended in RNA Secure (Ambion, Austin, Tex.). cDNA was generated by reverse transcribing approximately 2 µg of total RNA using Taqman7 reverse transcription reagents (AppliedBiosystems, Foster City, Calif.) according to manufacturers protocols. Subsequently, cDNA's were amplified with specific human cDNA primers, to CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2, using SYBR7 Green PCR master mix reagents (Applied Biosystems) according to manufacturers protocol. The level of copies of mRNA of these targets were evaluated by real-time PCR analysis using the BioRad Icycler and software (Hercules, Calif.).

Anti-Sera Preparation

The 15 amino acid peptides from chemokines CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 (Sequences 1 through 30) were synthesized (Sigma Genosys, The Woodlands, Tex.) and conjugated to hen egg lysozyme (Pierce, Rockford, Ill.) to generate the antigens for subsequent immunizations for anti-sera preparation or monoclonal antibody generation. The endotoxin levels of chemokine peptide conjugates were quantified by the chromogenic Limulus amebocyte lysate assay (Cape Cod, Inc., Falmouth, Miss.) and shown to be <5 EU/mg. 100 µg of the antigen was used as the immunogen together with complete Freund's adjuvant Ribi Adjuvant system (RAS) for the first immunization in a final volume of 1.0 ml. This mixture was administered in 100 ml aliquots on two sites of the back of the rabbit subcutaneously and 400 ml intramuscularly in each hind leg muscle. Three to four weeks later, rabbits received 100 µg of the antigen in addition to incomplete Freund's adjuvant for 3 subsequent immunizations. Anti-sera were collected when antibody titers reached 1:1,000,000. Subsequently, normal or anti-sera were heat-inactivated and diluted 1:50 in PBS.

Monoclonal Antibody Preparation

The 15 amino acid peptides from chemokines CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 (Sequences 1 through 30) were synthesized (Sigma Genosys) and conjugated to hen egg lysozyme (Pierce) to generate the antigens for subsequent immunizations for anti-sera preparation or monoclonal antibody generation. The endotoxin levels of chemokine peptide conjugates were quantified by the chromogenic Limulus amebocyte lysate assay (Cape Cod, Inc., Falmouth, Miss.) and shown to be <5 EU/mg. 100 µg of the antigen was used as the immunogen together with complete Freund's adjuvant Ribi Adjuvant system (RAS) for the first immunization in a final volume of 200 µl. This mixture was subcutaneously administered in 100 µl aliquots at two sites of the back of a rat, mouse, or immunoglobulin-humanized mouse. Two weeks later, animals received 100 µg of the antigen in addition to incomplete Freund's adjuvant for 3 subsequent immunizations. Serum were collected and when anti-CXCL9, -CXCL10, -CXCL11, -CCRL1, -CCRL2, -CCR5, -CCL1, -CCL2, -CCL3, -CCL4, -CCL4L1, -CCL5, -CCL7, -CCL8, -CCL14-1, -CCL14-2, -CCL14-3, -CCL15-1, -CCL15-2, -CCL16, -CCL19, -CCL23-1, -CCL23-2, -CCL24, -CCL26, -CCR6, -CCL20, and -CCL25, -CCL25-1, -CCL25-2 antibody titers reached 1:2,000,000, hosts were sacrificed and splenocytes were isolated for hybridoma generation.

B cells from the spleen or lymph nodes of immunized hosts were fused with immortal myeloma cell lines (e.g., YB2/0). Hybridomas were next isolated after selective culturing conditions (i.e., HAT-supplemented media) and limiting dilution methods of hybridoma cloning. Cells that produce antibodies with the desired specificity were selected using ELISA. Hybridomas from normal rats or mice were humanized with molecular biological techniques in common use. After cloning a high affinity and prolific hybridoma, antibodies were isolated from ascites or culture supernatants and adjusted to a titer of 1:2,000,000 and diluted 1:50 in PBS.

Anti-Sera or Monoclonal Antibody Treatment

Knockout or transgenic mice (8 to 12 weeks old, Charles River Laboratory, Wilmington, Mass.) that spontaneous—or when treated—develop inflammatory diseases were treated with 200 µl intraperitoneal injections of either anti-sera or monoclonal antibodies specific for each of the chemokines every three days. The inflammatory disease state of the host was next monitored for progression or regression of disease.

Cytokine Analysis by ELISA

The serum level of IL-2, -IL-6, -TNF-α, and -IFN-γ were determined by ELISA, following the manufacturers instructions (E-Biosciences, San Diego, Calif.). Plates were coated with 100 µl of the respective capture antibody in 0.1 M bicarbonate buffer (pH 9.5) and incubated 0/N at 4° C. After aspiration and washing with wash buffer, the wells were blocked with assay diluent for 1 hour at RT. Samples and standards were added and incubated for 2 hours at RT. Next, 100 µl of detection antibody solutions were added and incubated for 1 hour. 100 µl of avidin-HRP solution was added and incubated for 30 minutes. Subsequently, 100 µl Tetramethylbenzidine (TMB) substrate solution was added and allowed to react for 20 minutes. 500 of the stop solution was added and plates were read at 450 nm. The cytokine ELISA assays were capable of detecting >15 pg/ml for each assay.

Cytokine Analysis by Multiplex Cytokine ELISA

The T helper cell derived cytokines, IL-1α, IL-1β, IL-2, IL-12, IFN-γ, TNF-α, in serum were also determined by Beadlyte mouse multi-cytokine detection system kit provided by BioRad, following manufacturer instructions. Filter bottom plates were rinsed with 100 μl of bio-plex assay buffer and removal using a Millipore Multiscreen Separation Vacuum Manifold System (Bedford, Mass.), set at 5 in Hg. IL-1α, IL-1β, IL-2; IL-12, IFN-γ, TNF-α beads in assay buffer were added into wells. Next, 50 μl of serum or standard solution were added and the plates were incubated for 30 minutes at RT with continuous shaking (setting 3) using a Lab-Line Instrument Titer Plate Shaker (Melrose, Ill.), after sealing the plates. The filter bottom plates were washed 2 times, as before, and centrifuged at 300×g for 30 seconds. Subsequently, 50 μl of anti-mouse IL-1α, IL-1β, IL-2, IL-12, IFN-γ, TNF-α antibody-biotin reporter solution was added in each well followed by incubation with continuous shaking for 30 minutes followed by centrifugation at 300×g for 30 seconds. The plates were washed 3 times with 100 μl of bio-plex assay buffer as before. Next, 50 μl streptavidin-phycoerythrin solution was added to each well and incubated with continuous shaking for 10 minute at RT. 125 μl of bio-plex assay buffer was added and Beadlyte readings were measured using a Luminex1 instrument (Austin, Tex.). The resulting data was collected and calculated using Bio-plex1 software (Bio-Rad). The cytokine Beadlyte assays were capable of detecting >5 pg/ml for each analyte.

Serum Amyloid Protein A (BAA) ELISA

The SAA levels were determined by ELISA using a kit supplied by Biosource International, (Camarillo, Calif.). Briefly, 50 μl of SAA-specific monoclonal antibody solution was used to coat micro-titer strips to capture SAA. Serum samples and standards were added to wells and incubated for 2 hours at RT. After washing in the assay buffer, the HRP-conjugated anti-SAA monoclonal antibody solution was added and incubated for 1 hour at 37° C. After washing, 100 μl Tetramethylbenzidine (TMB) substrate solution was added and the reaction was stopped after incubation for 15 minutes at RT. After the stop solution was added, the plates were read at 450 nm.

Histology and Pathology Scoring

Fixed tissues were sectioned at 6 μm, and stained with hematoxylin and eosin for light microscopic examination. The intestinal lesions were multi-focal and of variable severity, the grades given to any section of intestine took into account the number of lesions as well as their severity. A score (0 to 4) was given, based on the following criteria: (Grade 0) no change from normal tissue. (Grade 1) 1 or a few multi-focal mononuclear cell infiltrates, minimal hyperplasia and no depletion of mucus. (Grade 2) lesions tended to involve more of the mucosa and lesions had several multi-focal, yet mild, inflammatory cell infiltrates in the lamina propria composed of mononuclear cells, mild hyperplasia, epithelial erosions were occasionally present, and no inflammation was noticed in the sub-mucosa. (Grade 3) lesions involved a large area of mucosa or were more frequent than Grade 2, where inflammation was moderate and often involved in the sub-mucosa as well as moderate epithelial hyperplasia, with a mixture of mononuclear cells and neutrophils. (Grade 4) lesions usually involved most of the section and were more severe than Grade 3 lesions. Additionally, Grade 4 inflammations were more severe and included mononuclear cell and neutrophils; epithelial hyperplasia was marked with crowding of epithelial cells in elongated glands. The summation of these score provide a total inflammatory disease score per mouse. The disease score could range from 0 (no change in any segment) to a maximum of 12 with Grade 4 lesions of segments.

Data Analysis

SigmaStat 2000 (Chicago, Ill.) software was used to analyze and confirm the statistical significance of data. The data were subsequently analyzed by the Student's t-test, using a two-factor, unpaired test. In this analysis, treated samples were compared to untreated controls. The significance level was set at $p<0.05$.

Results

Semiquantitative RT-PCR Identification of Molecular Targets

RT-PCR products obtained using CXCL9-, CXCL10-, CXCL11-, CCRL1-, CCRL2-, CCR5-, CCL1-, CCL2-, CCL3-, CCL4-, CCL4L1-, CCL5-, CCL7-, CCL8-, CCL14-1-, CCL14-2-, CCL14-3-, CCL15-1-, CCL15-2-, CCL16-, CCL19-, CCL23-1-, CCL23-2-, CCL24-, CCL26-, CCR6-, CCL20-, and CCL25-, CCL25-1-, CCL25-2-specific primer sets did not cross react with other gene targets due to exclusion of primers that annealed to host sequences 31-60. The primers used produced different size amplicon products relative the polymorphisms that resulted in CCL4 versus CCL4L1, CCL14-1, CCL14-2, versus CCL14-3, CCL15-1 versus CCL15-2, CCL23-1 versus CCL23-2, and CCL25, CCL25-1, versus CCL25-2. To this end, RT-PCR analysis of tissue from subjects exhibiting anaphylaxis, arthritis (e.g., rheumatoid, psoriatic), asthma, allergies (e.g., drug, insect, plant, food), atherosclerosis, delayed type hypersensitivity, dermatitis, diabetes (e.g., mellitus, juvenile onset), graft rejection, inflammatory bowel diseases (e.g., Crohn's disease, ulcerative colitis, enteritis), multiple sclerosis, myasthemia gravis, pneumonitis, psoriasis, nephritis, rhinitis, spondyloarthropathies, scheroderma, systemic lupus, or throiditis revealed that CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 were differentially expressed by inflammatory host cells.

In Vivo Inflammatory Disease Inhibition

Mammals that develop anaphylaxis, septic shock, arthritis (e.g., rheumatoid, psoriatic), asthma, allergies (e.g., drug, insect, plant, food), atherosclerosis, bronchitis, chronic pulmonary obstructive disease, delayed type hypersensitivity, dermatitis, diabetes (e.g., mellitus, juvenile onset), graft rejection, Grave's disease, Hashimoto's thyroiditis, inflammatory bowel diseases (e.g., Crohn's disease, ulcerative colitis, enteritis), interstitial cystitis, multiple sclerosis, myasthemia gravis, pneumonitis, psoriasis, nephritis, rhinitis, spondyloarthropathies, scheroderma, systemic lupus erythematosus, or throiditis were allowed to develop the inflammatory disease of interest. Antibodies directed against CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, or CCL25, CCL25-1, CCL25-2 differentially affected the progression and regression of inflammatory disease as determined by histological scoring and comparing pre- and post-treatment serum levels of IFN-γ, IL-1α, IL-1β, IL-6, IL-12, TNF-α, amyloid protein A. Antibodies directed towards CXCL9, CXCL-10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, or CCL25, CCL25-1, CCL25-2 effectively lead to the both regression and impeding progression of inflammatory disease as determined by histological scoring and comparing pre- and post-treatment serum levels of IFN-γ, IL-1α, IL-1β, IL-6, IL-12, TNF-α, amyloid protein A.

As indicated previously, the chemokines used in the methods of the invention are known. The assession numbers for the protein sequences are as follows:

CXCL9, (ACCESSION#NM_002416), CXCL10 (ACCESSION#NM_001565),

CXCL11 (ACCESSION#NM_005409), CCRL1 (ACCESSION#NM_016557),

CCRL2 (ACCESSION#NM_003965), CCR5 (ACCESSION#NM_060579),

CCL1 (ACCESSION#NM_002981), CCL2 (ACCESSION#NM_002982),

CCL3 (ACCESSION#XM_008450, NM_002983),

CCL4 (ACCESSION#NM_002984), CCL4L1 (ACCESSION#AY079147),

CCL5 (ACCESSION#NM_002985), CCL7 (ACCESSION#NM_006273),

CCL8 (ACCESSION#NM_005623), CCL14-1 (ACCESSION#NM_004166),

CCL14-2 (ACCESSION#NM_032962),

CCL14-3 (ACCESSION#NM_032963),

CCL15-1 (ACCESSION#NM_032964),

CCL15-2 (ACCESSION#NM_004167),

CCL16 (ACCESSION#NM_004590), CCL19 (ACCESSION#NM_006274),

CCL23-1 (ACCESSION#NM_005064),

CCL23-2 (ACCESSION#NM_145898),

CCL24 (ACCESSION#NM_002991), CCL26 (ACCESSION#NM_006072),

CCR6 (ACCESSION#U45984), CCL20 (ACCESSION#NM_004591)

CCL25 (ACCESSION#015444), CCL25-1 (ACCESSION#NM_005624), and CCL25-2 (ACCESSION#NM_148888).

For the cDNA sequences, the following GenBank accession numbers apply:

CXCL9 (ACCESSION#NM_002416), CXCL10 (ACCESSION#NM_001565),

CXCL11 (ACCESSION#NM_005409), CCRL1 (ACCESSION#NM_016557),

CCRL2 (ACCESSION#NM_003965), CCR5 (ACCESSION#NM_000579),

CCL1 (ACCESSION#NM_002981), CCL2 (ACCESSION#NM_002982),

CCL3 (ACCESSION#XM_008450, NM_002983),

CCL4 (ACCESSION#NM_002984), CCL4L1 (ACCESSION#AY079147),

CCL5 (ACCESSION#NM_002985), CCL7 (ACCESSION#NM_006273),

CCL8 (ACCESSION#NM_005623), CCL14-1 (ACCESSION#NM_004166),

CCL14-2 (ACCESSION#NM_032962), CCL14-3 (ACCESSION#NM_032963),

CCL15-1 (ACCESSION#NM_032964),

CCL15-2 (ACCESSION#NM_004167),

CCL16 (ACCESSION#NM_004590), CCL19 (ACCESSION#NM_006274),

CCL23-1 (ACCESSION#NM_005064),

CCL23-2 (ACCESSION#NM_145898),

CCL24 (ACCESSION#NM_002991), CCL26 (ACCESSION#NM_006072),

CCR6 (ACCESSION#U45984), CCL20 (ACCESSION#NM_004591),

CCL25 (ACCESSION#015444), CCL25-1 (ACCESSION#NM_005624),

As shown in the table, the particular chemokines which give rise to inflammatory diseases differ with the disease. They also differ among individuals. Hence, it is wise, when treating an individual, to identify the particular chemokines which are increased in the tissues of the patient. Using the antibodies produced against each of the chemokines and exposing the tissue samples from the patient to the particular antibodies, then evaluating the amount of antibody/chemokine binding, it is possible to evaluate the level of expression for each chemokine and to administer to the patient the particular antibodies that will bind the excessive chemokine. This tailored approach to treatment of inflammatory disease is novel, and a particularly valuable aspect of the invention.

TABLE 1

Chemokine, Chemokine Receptor and Inflammatory Disease Association (dependent of stage of disease)

| Disease | Chemokine | Chemokine Receptor |
|---|---|---|
| Allergies (Skin, Food & Respiratory) | CCL1, CCL2, CCL5, CCL7, CCL8, CCL11, CCL13, CCL17, CCL22, CCL24, CCL25, CCL26 | CCR3, CCR4, CCR8, CCR9 |
| Asthma | CCL3, CCL4, CCL5, CCL7, CCL8, CCL11, CCL15, CCL17, CCL22, CCL24, CCL26, | CCR3, CCR4, CCR5, |
| Septic Shock, Anaphylaxis | CXCL1, CXCL2, CXCL3, CXCL5, CXCL6, CXCL7, CXCL8, CXCL9, CXCL10, CXCL11, CCL5 | CXCR1, CXCR2, CXCR3 |
| Arthritis (septic, rheumatoid, psoriatic) | CXCL9, CXCL10, CXCL11, CXCL12, CXCL13 | CXCR3, CXCR4, CXCR5 |
| | CCL20 | CCR6 |
| | XCL1 | XCR1 |
| | CX3CL1 | CX3CR1 |

TABLE 1-continued

Chemokine, Chemokine Receptor and Inflammatory Disease Association (dependent of stage of disease)

| Disease | Chemokine | Chemokine Receptor |
|---|---|---|
| Osteoarthritis | CXCL1, CXCL2, CXCL3, CXCL5, CXCL6, CXCL7, CXCL8, CXCL12, CXCL13, | CXCR1, CXCR2, |
| | CCL2, CCL3, CCL4, CCL7, CCL8, CCL13, CCL5, CCL18 | CCR2, CCR5 |
| Atherosclerosis | CXCL1, CXCL2, CXCL3, CXCL4, CXCL5, CXCL8 | CXCR1, CXCR2 |
| | CCL2, CCL3, CCL4, CCL8, CCL12, CCL13, CCL17, CCL22 | CCR2, CCR8 |
| | CX3CL1 | CX3CR1 |
| Dermatitis & Delayed-Typed Hypersensitivity | CXCL9, CXCL10, CXCL11, | CXCR3 |
| | CCL2, CCL3, CCL4, CCL5, CCL17, CCL20, CCL22, CCL27 | CCR4, CCR5, CCR6, CCR10 |
| Diabetes | CXCL9, CXCL10, CXCL11, | CXCR3 |
| | CCL2, CCL9 | CCR2, CCR4 |
| | CX3CL1 | CX3CR1 |
| Graft rejection | CXCL9, CXCL10, CXCL11, | CXCR3 |
| | CCL3, CCL4, CCL5 | CCR5 |
| | XCL1 | XCR1 |
| Inflammatory Bowel Diseases | CXCL9, CXCL10, CXCL11, | CXCR3 |
| | CCL3, CCL4, CCL5 | CCR5 |
| Interstitial Cystitis | CXCL9, CXCL10, CXCL11, | CXCR3 |
| | CCL3, CCL4, CCL5 | CCR5 |
| Multiple Sclerosis | CXCL9, CXCL10, CXCL11, | CXCR3 |
| | CCL3, CCL4, CCL5, CCL7, CCL14, CCL15, CCL23 | CCR1, CCR5 |
| Myasthemia gravis, Grave's disease, & Hashimoto thyroiditis | CXCL9, CXCL10, CXCL11, | CXCR3 |
| | CCL3, CCL4, CCL5 | CCR5 |
| | XCL1 | XCR1 |
| Nephritis & Systemic Lupus Erthematosus | CXCL9, CXCL10, CXCL11, CXCL13 | CXCR3, CXCR5 |
| | CCL2, CCL3, CCL4, CCL5, CCL8, CCL12, CCL13, | CCR2, CCR4 |
| | CX3CL1 | CX3CR1 |
| Pneumonitis, Chronic Obstructive Pulmonary Disease, & Chronic Bronchitis | CXCL1, CXCL2, CXCL3, CXCL5, CXCL7, CXCL8 | CXCR2, CXCR3 |
| | CCL3, CCL5, CCL7, CCL8, CCL11, CCL13, CCL24, CCL26 | CCR3 |

The method consists of 1) exposing tissues from a mammal suffering from and inflammatory condition to several differing antibodies which bind to specific chemokines, 2) identifying level of expression of each chemokine based on binding of the each of the differing antibodies, and 3) administering to said mammal those specific antibodies which bind to the over-expressed chemokines. Additionally, the level of expression of any particular chemokine may be determined using PCR, as disclosed herein.

Antibodies of the invention may be administered directly to target tissue. For example, compositions containing the compositions containing antibodies as prepared under the heading "anti-sera preparation" can be administered intravenously, rectally vaginally, intrathecally, by inhalation, transvaginally, transurethrally or directly to tissue during surgery. The anti-sera preparations may also be placed on a solid support such as a sponge or gauze for administration to the mucosa. The antibodies may also be administered using microspheres or liposomes. The compositions for administration are prepared in the usual pharmaceutically acceptable carriers such as saline, water, buffered saline, glucose in saline, etc.

Liquid compositions will most often be prepared containing 0.1 to 1000 μg of antibody in each ml of solution. All compositions will be administered in an inflammatory inhibiting effective amount with the amount of dosage given depending on the size and condition of the individual in need of anti-inflammatory treatment.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method of treating a mammal with inflammatory disease, comprising:
    a) exposing a tissue sample from said mammal to an antibody which binds specifically to CCL25;
    b) determining a level of expression of CCL25 based on binding of said antibody to said tissue sample; and
    c) if over-expression of CCL25 is detected in said tissue sample of said mammal, administering to said mammal an effective amount of an antibody which binds specifically to CCL25 for the treatment of said inflammatory disease is selected from the group consisting of septic shock, interstitial cystitis, and nephritis.

2. The method of claim 1, wherein said mammal is a human.

3. The method of claim 1, wherein in step c, said antibody or antibodies are humanized antibodies.

4. The method of claim 1, wherein in step c, said antibody or antibodies are chimeric antibodies.

5. The method of claim 1, wherein in step c, said antibody or antibodies are administered directly into an inflamed tissue.

6. The method of claim 1, wherein in step c, said antibody or antibodies are administered parenterally.

7. The method of claim 1, wherein in step c, said antibody or antibodies are administered systemically.

8. The method of claim 1, wherein in step c, said antibody or antibodies are administered in a liquid carrier.

9. The method of claim 1, wherein in step c, said antibody or antibodies are administered on a solid support.

10. A method of treating a mammal with inflammatory disease, comprising:
   a) determining the level of CCL25 in a tissue sample in said mammal using PCR; and
   b) if over-expression of CCL25 is detected in said tissue sample of said mammal, administering to said mammal an effective amount of an antibody which binds specifically to CCL25 for the treatment of said inflammatory disease, wherein said inflammatory disease is selected from the group consisting of septic shock, interstitial cystitis and nephritis.

11. The method of claim 10, wherein said antibody or antibodies are administered directly into an inflamed tissue.

12. The method of claim 10, wherein said antibody or antibodies are administered systemically.

13. The method of claim 10, wherein in step c, said antibody or antibodies are administered parenterally.

14. The method of claim 10, wherein said antibody or antibodies are administered on a solid support.

15. The method of claim 10, wherein said antibody or antibodies are human or humanized antibodies.

16. The method of claim 10, wherein in step c, said antibody or antibodies are chimeric antibodies.

* * * * *